United States Patent
Kim et al.

(10) Patent No.: US 7,824,780 B2
(45) Date of Patent: Nov. 2, 2010

(54) IMIDAZOPYRIMIDINE-BASED COMPOUND AND ORGANIC LIGHT-EMITTING DEVICE EMPLOYING ORGANIC LAYER INCLUDING THE SAME

(75) Inventors: Hee-Yeon Kim, Suwon-si (KR); Seung-Gak Yang, Suwon-si (KR); Jung-Han Shin, Suwon-si (KR); Chang-Ho Lee, Suwon-si (KR); Hee-Joo Ko, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 441 days.

(21) Appl. No.: 12/028,744

(22) Filed: Feb. 8, 2008

(65) Prior Publication Data
US 2008/0226945 A1    Sep. 18, 2008

(30) Foreign Application Priority Data
Mar. 13, 2007    (KR)    .................. 10-2007-0024697

(51) Int. Cl.
*H01L 51/54*    (2006.01)
*C07D 487/04*    (2006.01)
(52) U.S. Cl. .................. 428/690; 428/917; 544/281; 313/504; 313/506
(58) Field of Classification Search .................. None
See application file for complete search history.

(56) References Cited

U.S. PATENT DOCUMENTS

| 4,356,429 | A | 10/1982 | Tang |
| 6,559,256 | B2 | 5/2003 | Holmes et al. |
| 6,620,529 | B1 | 9/2003 | Ise et al. |

FOREIGN PATENT DOCUMENTS

| EP | 1 582 516 A1 | 10/2005 |
| JP | 11-329734 | 11/1999 |
| JP | 2005-220136 | 8/2005 |
| KR | 10-2005-0078472 | 8/2005 |
| WO | WO 2007/069847 A1 | 6/2007 |

OTHER PUBLICATIONS

Kuwabara et al., Advanced Materials, vol. 6, Issue 9, pp. 677-679.*
European Search Report dated Jun. 24, 2008, for European application 08102100.8, indicating relevance of listed references in this IDS.
Ebisawa, A., et al., *Anthracenes and organic electroluminescent devices using them as electron-injecting and -transporting agents*, Chemical Abstracts Service, Columbus, Ohio (2008), XP 002481489 (On Order).

(Continued)

*Primary Examiner*—Dawn Garrett
(74) *Attorney, Agent, or Firm*—Christie, Parker & Hale, LLP (57) ABSTRACT

Imidazopyrimidine-based compounds and organic light-emitting devices employing organic layers including the imidazopyrimidine-based compounds are provided. Organic light-emitting devices employing organic layers including the imidazopyrimidine-based compounds feature low driving voltages, high efficiency, high brightness, long lifetimes, and low power consumption.

15 Claims, 1 Drawing Sheet

OTHER PUBLICATIONS

Ebisawa, A., et al., *Anthracenes and organic electroluminescent devices using them as electron-injecting and -transporting agents*, Chemical Abstracts Service, Columbus, Ohio (2008), 2 pages, XP 002481489.

Adachi, C., et al., *Endothermic energy transfer: A mechanism for generating very efficient high-energy phosphorescent emission in organic materials*, Applied Physics Letters, vol. 79, No. 13, Sep. 24, 2001, pp. 2082-2084.

Adachi, et al., Appl. Phys. Lett., 79, pp. 2082-2084 (2001).

Patent Abstracts of Japan, Publication No. 11-329734, Published on Nov. 30, 1999, in the name of Sato, et al.

Patent Abstracts of Japan, Publication No. 2005-220136, Published on Aug. 18, 2005, in the name of Lee, et al.

* cited by examiner

FIG. 1

IMIDAZOPYRIMIDINE-BASED COMPOUND AND ORGANIC LIGHT-EMITTING DEVICE EMPLOYING ORGANIC LAYER INCLUDING THE SAME

CROSS-REFERENCE TO RELATED PATENT APPLICATION

This application claims priority to and the benefit of Korean Patent Application No. 10-2007-0024697, filed on Mar. 13, 2007 in the Korean Intellectual Property Office, the entire content of which is incorporated herein by reference.

BACKGROUND OF THE INVENTION

1. Field of the Invention

The present invention relates to imidazopyrimidine-based compounds and to organic light-emitting devices employing organic layers including the compounds. More particularly, the present invention relates to an imidazopyrimidine-based compound for use in an electron transport layer of an organic light-emitting device.

2. Description of the Related Art

Organic light-emitting devices (OLEDs) are self-emitting devices having wide viewing angles, good contrast, and rapid response speeds. OLEDs can create full-color images.

Generally, an organic light-emitting device is structured by sequentially stacking an anode, a hole transport layer, an emitting layer, an electron transport layer, and a cathode on a substrate. The hole transport layer, the emitting layer, and the electron transport layer are organic thin layers made of organic compounds.

Organic light-emitting devices having the above-described structure are operated as follows. When voltages are applied to the anode and cathode, holes from the anode are transported to an emitting layer via a hole transport layer, and electrons from the cathode are transported to the emitting layer via an electron transport layer. Carriers, such as the holes and the electrons, are recombined in the emitting layer to thereby generate excitons. When the excitons move from an excited state to a ground state, fluorescent molecules of the emitting layer emit light. Heteroaromatic compounds, such as oxadiazoles and thiadiazoles, are known as electron transport layer materials.

However, conventional organic light-emitting devices have unsatisfactory driving voltages, brightness, current density, power efficiency, and lifetime characteristics.

SUMMARY OF THE INVENTION

According to one embodiment of the present invention, an imidazopyrimidine-based compound has good electron transport capabilities.

In another embodiment of the present invention, an organic light-emitting device uses the imidazopyrimidine-based compound and has high efficiency, low driving voltage, high brightness, and long lifetime characteristics.

According to an embodiment of the present invention, an imidazopyrimidine-based compound is represented by Formula 1.

Formula 1

In Formula 1, each of p and q is independently an integer ranging from 1 to 5, and m and n are each independently an integer ranging from 0 to 4 provided that the sum of m and n is not zero (0). Each of $R_1$, $R_2$, $R_3$, $R_4$, $R_5$, $R_6$, $R_7$, $R_8$, $R_9$, and $R_{10}$ is independently selected from hydrogen, halogens, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_1$-$C_{30}$ acyl groups, substituted and unsubstituted $C_2$-$C_{30}$ alkenyl groups, substituted and unsubstituted $C_2$-$C_{30}$ alkynyl groups, substituted and unsubstituted $C_6$-$C_{30}$ aryl groups, and substituted and unsubstituted $C_3$-$C_{30}$ heteroaryl groups. Two or more adjacent groups selected from $R_4$ through $R_6$ may be joined together to form a saturated or unsaturated ring. Two or more adjacent groups selected from $R_8$ through $R_{10}$ may be joined together to form a saturated or unsaturated ring. Each of $L_1$ and $L_2$ is independently selected from single bonds, substituted and unsubstituted $C_1$-$C_{30}$ alkylene groups, substituted and unsubstituted $C_6$-$C_{30}$ arylene groups, and substituted and unsubstituted $C_3$-$C_{30}$ heteroarylene groups. Each of $Ar_1$ and $Ar_2$ is independently selected from substituted and unsubstituted $C_6$-$C_{30}$ aryl groups and substituted and unsubstituted $C_3$-$C_{30}$ heteroaryl groups.

According to another embodiment of the present invention, an organic light-emitting device includes a first electrode, a second electrode, and an organic layer between the first electrode and second electrode. The organic layer includes the imidazopyrimidine-based compound.

The imidazopyrimidine-based compounds of Formula 1 have good electron transport capabilities. Thus, organic light-emitting devices employing organic layers including the imidazopyrimidine-based compounds can have low driving voltages, high current densities, high brightness, high efficiency, and long lifetimes.

BRIEF DESCRIPTION OF THE DRAWINGS

The above and other features and advantages of the present invention will be better understood by reference to the following detailed description when considered in conjunction with the attached drawing in which.

DETAILED DESCRIPTION OF THE INVENTION

According to one embodiment of the present invention, an imidazopyrimidine-based compound is represented by Formula 1.

For example, each of $R_1$ through $R_{10}$ may be independently selected from hydrogen, substituted and unsubstituted $C_1$-$C_{10}$ alkyl groups, substituted and unsubstituted $C_2$-$C_{10}$ alkenyl groups, substituted and unsubstituted $C_6$-$C_{12}$ aryl groups, and substituted and unsubstituted $C_3$-$C_{12}$ heteroaryl groups.

Two or more adjacent groups selected from $R_4$ through $R_6$, or two or more adjacent groups selected from $R_8$ through $R_{10}$ may be joined together to form a substituted or unsubstituted $C_6$-$C_{12}$ aromatic ring, but the groups are not limited thereto.

In Formula 1, each of $L_1$ and $L_2$ is independently selected from single bonds, substituted and unsubstituted $C_1$-$C_{30}$ alkylene groups, substituted and unsubstituted $C_6$-$C_{30}$ arylene groups, and substituted and unsubstituted $C_3$-$C_{30}$ heteroarylene groups. For example, each of $L_1$ and $L_2$ may be independently selected from substituted and unsubstituted Formula 1

$C_6$-$C_{12}$ arylene groups, and substituted and unsubstituted $C_3$-$C_{12}$ heteroarylene groups, but are not limited thereto.

In Formula 1, each of $Ar_1$ and $Ar_2$ is independently selected from substituted and unsubstituted $C_6$-$C_{30}$ aryl groups, and substituted and unsubstituted $C_3$-$C_{30}$ heteroaryl groups. For example, each of $Ar_1$ and $Ar_2$ may be independently selected from substituted and unsubstituted $C_6$-$C_{12}$ aryl groups, and substituted and unsubstituted $C_3$-$C_{12}$ heteroaryl groups.

In Formula 1, each of p and q is an integer ranging from 1 to 5. In one embodiment, for example, each of p and q is an integer ranging from 1 to 3. That is, at least one imidazopyrimidine ring is connected to $L_1$ or $L_2$, and the number of imidazopyrimidine rings may be determined according to the chemical structure of $L_1$ or $L_2$.

In Formula 1, each of m and n is an integer ranging from 0 to 4. However, the sum of m and n is not zero (0). That is, at least one of the 1- to 8-positions of the anthracene ring is connected to the imidazopyrimidine ring. For example, m may be 0, and n may be 1. Alternatively, each of m and n may be 1.

Nonlimiting examples of suitable unsubstituted $C_1$-$C_{30}$ alkyl groups for use in Formula 1 include methyl groups, ethyl groups, propyl groups, isobutyl groups, sec-butyl groups, pentyl groups, iso-amyl groups, and hexyl groups. At least one hydrogen atom of the alkyl group may be substituted by a substituent selected from halogens, hydroxyl groups, nitro groups, cyano groups, amino groups, amidino groups, hydrazines, hydrazones, carboxyl groups and its salts, sulfonyl groups and its salts, phosphonyl groups and its salts, $C_1$-$C_{30}$ alkyl groups, $C_1$-$C_{30}$ alkenyl groups, $C_1$-$C_{30}$ alkynyl groups, $C_6$-$C_{30}$ aryl groups, $C_7$-$C_{20}$ arylalkyl groups, $C_2$-$C_{20}$ heteroaryl groups, and $C_3$-$C_{30}$ heteroarylalkyl groups.

According to Formula 1, an imidazopyrimidine ring is connected to at least one of the 1- to 8-positions of an anthracene ring via a linking group $L_1$ or $L_2$.

The 9- and 10-positions of the anthracene ring are structurally weak points. Thus, if a functional group is introduced at the 9- and 10-positions of the anthracene ring, it may be easily separated from the anthracene ring due to heat, oxygen, moisture, or the like. For example, if an electron-deficient imidazopyrimidine ring is connected at the 9- or 10-position of the anthracene ring, the imidazopyrimidine ring is easily separated from the anthracene ring due to heat or the like generated during the formation (e.g., deposition) of an organic layer of an organic light-emitting device or during the operation of the organic light-emitting device, thereby lowering device characteristics. In an imidazopyrimidine-based compound according to the present invention, however, an aromatic ring, such as an aryl group or a heteroaryl group, is introduced at the 9- and 10-positions of an anthracene ring, and an electron-deficient imidazopyrimidine ring is introduced at at least one of the 1- to 8-positions of the anthracene ring, thereby improving the structural stability and electron mobility of the compound.

In Formula 1, each of $R_1$, $R_2$, $R_3$, $R_4$, $R_5$, $R_6$, $R_7$, $R_8$, $R_9$, and $R_{10}$ is independently selected from hydrogen, halogens, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_1$-$C_{30}$ acyl groups, substituted and unsubstituted $C_2$-$C_{30}$ alkenyl groups, substituted and unsubstituted $C_2$-$C_{30}$ alkynyl groups, substituted and unsubstituted $C_6$-$C_{30}$ aryl groups, and substituted and unsubstituted $C_3$-$C_{30}$ heteroaryl groups. Two or more adjacent groups selected from $R_4$ through $R_6$ may be joined together to form a saturated or unsaturated ring, and two or more adjacent groups selected from $R_8$ through $R_{10}$ may be joined together to form a saturated or unsaturated ring.

Nonlimiting examples of suitable unsubstituted $C_1$-$C_{30}$ alkoxy groups for use in Formula 1 include methoxy groups, ethoxy groups, phenyloxy groups, cyclohexyloxy groups, naphthyloxy groups, isopropyloxy groups, and diphenyloxy groups. At least one hydrogen atom of the alkoxy group may be substituted by a substituent selected from those listed above in connection with the alkyl group.

Nonlimiting examples of suitable unsubstituted $C_1$-$C_{30}$ acyl groups for use in Formula 1 include acetyl groups, ethylcarbonyl groups, isopropylcarbonyl groups, phenylcarbonyl groups, naphthylenecarbonyl groups, diphenylcarbonyl groups, and cyclohexylcarbonyl groups. At least one hydrogen atom of the acyl group may be substituted by a substituent selected from those listed above in connection with the alkyl group.

The unsubstituted $C_2$-$C_{30}$ alkenyl group in Formula 1 refers to an alkyl group as defined above that contains a carbon-carbon double bond at the center or an end of the alkyl group. Nonlimiting examples of suitable alkenyl groups include ethylene groups, propylene groups, butylene groups, and hexylene groups. At least one hydrogen atom of the alkenyl group may be substituted by a substituent selected from those listed above in connection with the alkyl group.

The unsubstituted $C_2$-$C_{30}$ alkynyl group in Formula 1 refers to an alkyl group as defined above that contains a carbon-carbon triple bond at the center or an end of the alkyl group. Nonlimiting examples of suitable alkynyl groups include acetylene groups, propylene groups, phenylacetylene groups, naphthylacetylene groups, isopropylacetylene groups, t-butylacetylene groups, and diphenylacetylene groups. At least one hydrogen atom of the alkynyl group may be substituted by a substituent selected from those recited above in connection with the alkyl group.

The unsubstituted $C_6$-$C_{30}$ aryl group used in Formula 1 refers to a carbocyclic aromatic system of 6-30 carbon atoms containing at least one aromatic ring. Two or more aromatic rings may be fused to each other or may be connected by a single bond or the like. At least one hydrogen atom of the aryl group may be substituted by a substituent selected from those listed above in connection with the alkyl group.

Nonlimiting examples of the substituted or unsubstituted $C_6$-$C_{30}$ aryl group include phenyl groups, $C_1$-$C_{10}$ alkylphenyl groups (e.g., ethylphenyl groups), $C_1$-$C_{10}$ alkylbiphenyl groups (e.g., ethylbiphenyl groups), halophenyl groups (e.g., o-, m- and p-fluorophenyl groups, dichlorophenyl groups), dicyanophenyl groups, trifluoromethoxyphenyl groups, o-, m-, and p-tolyl groups, o-, m-, and p-cumenyl groups, mesityl groups, phenoxyphenyl groups, (α,α-dimethylbenzyl)phenyl groups, (N,N'-dimethyl)aminophenyl groups, (N,N'-diphenyl)aminophenyl groups, pentalenyl groups, indenyl groups, naphthyl groups, halonaphthyl groups (e.g., fluoronaphthyl groups), $C_1$-$C_{10}$ alkylnaphthyl groups (e.g., methyinaphthyl groups), $C_1$-$C_{10}$ alkoxynaphthyl groups (e.g., methoxynaphthyl groups), anthracenyl groups, azulenyl groups, heptalenyl groups, acenaphthylenyl groups, phenalenyl groups, fluorenyl groups, anthraquinolyl groups, methylanthryl groups, phenanthryl groups, triphenylenyl groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_3$-$C_{30}$ heteroaryl group used in Formula 1 refers to a system having at least one aromatic ring containing at least one heteroatom selected from N, O, P, and S. Two or more aromatic rings may be fused to each other or may be connected by a single bond or the like. At least one hydrogen atom of the heteroaryl group may be substituted by a substituent selected from those listed above in connection with the alkyl group.

Nonlimiting examples of the unsubstituted $C_3$-$C_{30}$ heteroaryl group used in Formula 1 include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups.

In more detail, nonlimiting examples of suitable substituents for $R_1$ through $R_{10}$ in Formula 1 include hydrogen, $C_1$-$C_{10}$ alkyl groups, $C_1$-$C_{10}$ haloalkyl groups, $C_2$-$C_{10}$ alkenyl groups, $C_2$-$C_{10}$ haloalkenyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

In Formula 1, nonlimiting examples of suitable substituents for $L_1$ and $L_2$ include phenylene groups, halophenylene groups, $C_1$-$C_{10}$ alkylphenylene groups, $C_1$-$C_{10}$ alkoxyphenylene groups, naphthylene groups, halonaphthylene groups, $C_1$-$C_{10}$ alkylnaphthylene groups, and $C_1$-$C_{10}$ alkoxynaphthylene groups.

In Formula 1, nonlimiting examples of suitable substituents for $Ar_1$ and $Ar_2$ include phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, $C_1$-$C_{10}$ alkoxynaphthyl groups, pyridinyl groups, halopyridinyl groups, $C_1$-$C_{10}$ alkylpyridinyl groups, $C_1$-$C_{10}$ alkoxypyridinyl groups, quinolinyl groups, haloquinolinyl groups, $C_1$-$C_{10}$ alkylquinolinyl groups, $C_1$-$C_{10}$ alkoxyquinolinyl groups, isoquinolinyl groups, haloisoquinolinyl groups, $C_1$-$C_{10}$ alkylisoquinolinyl groups, and $C_1$-$C_{10}$ alkoxyisoquinolinyl groups.

Nonlimiting examples of suitable compounds satisfying Formula 1 include Compounds 1 through 9.

Compound 1

Compound 2

Compound 3

Compound 4

Compound 5

-continued

Compound 6

Compound 7

Compound 8

Compound 9

The imidazopyrimidine-based compounds of Formula 1 can be synthesized using any suitable method.

For example, an imidazopyrimidine-based compound of Formula 1 can be obtained by reacting a compound represented by Formula 2 below with a compound represented by Formula 3 below and/or a compound represented by Formula 4 below.

In Formulae 2 through 4, $R_1$ through $R_{10}$, $L_1$, $L_2$, $Ar_1$, $Ar_2$, p, q, n, and m are as defined above in connection with Formula 1. The above synthesis method can be performed using a Suzuki reaction.

The imidazopyrimidine-based compounds of Formula 1 as described above can be used in organic layers of organic light-emitting devices. In detail, according to one embodiment of the present invention, an organic light-emitting device includes a first electrode, a second electrode, and an organic layer between the first and second electrodes. The organic layer includes an imidazopyrimidine-based compound of Formula 1. In one embodiment, the organic layer may be an electron transport layer. The organic light-emitting device may further include at least one of a hole injection layer, a hole transport layer, an electron blocking layer, an emitting layer, a hole blocking layer, an electron transport layer, and an electron injection layer. For example, when the organic layer including the imidazopyrimidine-based compound of Formula 1 is an electron transport layer, the organic light-emitting device according to one embodiment of the present invention may further include a hole injection layer, a hole transport layer, an emitting layer, and an electron injection layer. Moreover, when forming an emitting layer using a phosphorescent material, the organic light-emitting device according to one embodiment of the present invention may further include a hole blocking layer. In addition, various modifications can be made.

Figure 1:
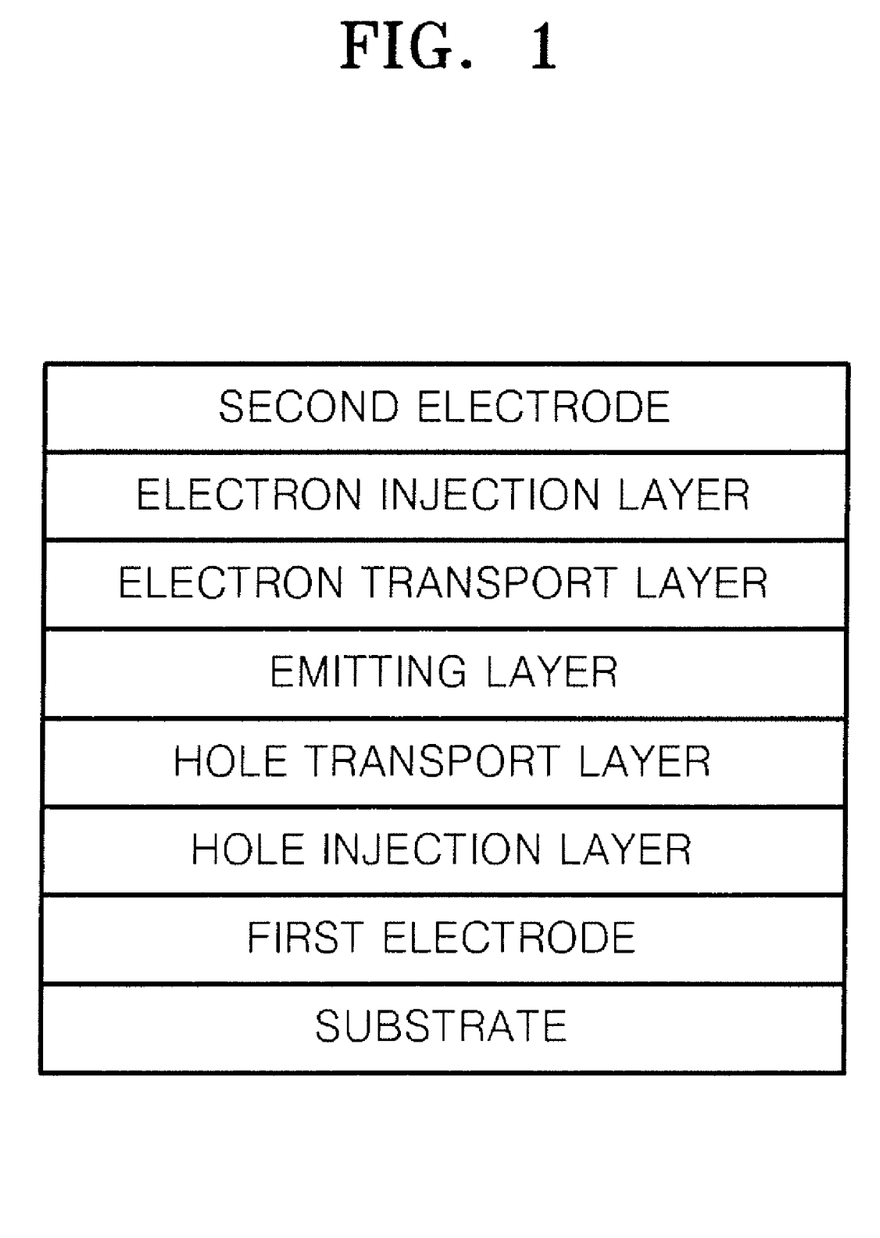
FIG. 1 is a schematic view of an organic light-emitting device according to an embodiment of the present invention.

In more detail, an organic light-emitting device according to an embodiment of the present invention is illustrated in FIG. 1. Referring to FIG. 1, an organic light-emitting device has a first electrode/hole injection layer/hole transport layer/emitting layer/electron transport layer/electron injection layer/second electrode structure. In addition, an organic light-emitting device according to another embodiment of the present invention may have a first electrode/hole injection layer/emitting layer/electron transport layer/electron injection layer/second electrode structure, or a first electrode/hole injection layer/hole transport layer/emitting layer/hole blocking layer/electron transport layer/electron injection layer/second electrode structure, but is not limited thereto. Here, the electron transport layer may include a compound of Formula 1.

An emitting layer of an organic light-emitting device according to the present invention may include a phosphorescent or fluorescent dopant generating red, green, blue, or white light. The phosphorescent dopant may be an organometallic compound including at least one element selected from Ir, Pt, Os, Ti, Zr, Hf, Eu, Tb, and Tm.

A method of manufacturing an organic light-emitting device according to an embodiment of the present invention will now be described with reference to FIG. 1. First, a first electrode is formed on a substrate by deposition or sputtering using a first electrode material having a high work function. The first electrode may be an anode or a cathode. Here, the substrate may be any substrate commonly used in organic light-emitting devices. In one embodiment, the substrate may be a glass or transparent plastic substrate having good mechanical strength, thermal stability, transparency, surface smoothness, handling properties, and water repulsion. The first electrode material may be a material having good conductivity, nonlimiting examples of which include indium tin oxide (ITO), indium zinc oxide (IZO), tin oxide ($SnO_2$), zinc oxide (ZnO), Al, Mg, or Ag. The first electrode may be a transparent electrode, a translucent electrode, or a reflective electrode.

Next, a hole injection layer (HIL) may be formed on the first electrode using any one of various methods, e.g., vacuum deposition, spin-coating, casting, or Langmuir-Blodgett (LB) techniques.

When forming the hole injection layer by vacuum deposition, the deposition conditions vary according to the type of hole injection layer material, the structure and thermal characteristics of the hole injection layer, etc. However, in one embodiment, the hole injection layer is deposited at a deposition rate ranging from about 0.01 to about 100 Å/sec, a temperature ranging from about 100 to about 500° C., and a vacuum pressure ranging from about $10^{-8}$ to about $10^{-3}$ torr.

When forming the hole injection layer by spin-coating, the coating conditions vary according to the type of hole injection layer material, the structure and thermal characteristics of the hole injection layer, etc. However, in one embodiment, the spin-coating is performed at a coating speed ranging from about 2,000 to about 5,000 rpm, and, after the spin-coating, thermal treatment is performed at a temperature ranging from about 80 to about 200° C. to remove solvent.

The hole injection layer material is not particularly limited and may be any known hole injection layer material. Nonlimiting examples of suitable hole injection layer materials include phthalocyanine compounds (e.g., copper phthalocyanine), Starburst-type amine derivatives (e.g., TCTA, m-MTDATA, m-MTDAPB), soluble conductive polymers, e.g., polyaniline/dodecylbenzenesulfonic acid (Pani/DBSA), poly (3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS).

TCTA m-MTDATA

TPD

α-NPD

The hole injection layer may be formed to a thickness ranging from about 100 to about 10,000 Å. In one embodiment, for example, the hole injection layer is formed to a thickness ranging from about 100 to about 1,000 Å. When the thickness of the hole injection layer is within these ranges, proper hole injection characteristics can be obtained and increases in driving voltage can be substantially prevented.

Next, a hole transport layer (HTL) may be formed on the hole injection layer using various methods, e.g., vacuum deposition, spin-coating, casting, or LB techniques. When forming the hole transport layer using vacuum deposition or spin-coating, the deposition or coating conditions vary according to the type of compound used, but are generally the same as those for the formation of the hole injection layer.

The hole transport layer material is not particularly limited and may be any known hole transport layer material, e.g., carbazole derivatives (such as N-phenylcarbazole or polyvinylcarbazole), amine derivatives having a fused aromatic ring (such as N,N'-bis(3-methylphenyl)-N,N'-diphenyl-[1,1-biphenyl]-4,4'-diamine (TPD) or N,N'-di(naphthalene-1-yl)-N, N'-diphenylbenzidine (α-NPD)), and the like.

The hole transport layer may be formed to a thickness ranging from about 50 to about 1,000 Å. In one embodiment, for example, the hole transport layer may be formed to a thickness ranging from about 100 to about 600 Å. When the thickness of the hole transport layer is within these ranges, proper hole transport characteristics can be obtained and increases in driving voltage can be substantially prevented.

Next, an emitting layer (EML) may be formed on the hole transport layer using vacuum deposition, spin-coating, casting, or LB techniques. When forming the emitting layer using vacuum deposition or spin-coating, the deposition or coating conditions vary according to the type of compound used, but are generally the same as those for the formation of the hole injection layer.

The emitting layer may be formed using any known emitting material. The emitting layer may also be formed using any known host and dopant. With respect to the dopant, known fluorescent dopants and known phosphorescent dopants can be used. Nonlimiting examples of suitable hosts include Alq$_3$, 4,4'-N,N'-dicarbazole-biphenyl (CBP), poly(n-vinylcarbazole) (PVK), distyrylarylene (DSA), and the like.

Nonlimiting examples of suitable dopants include Ir(ppy)$_3$(ppy=phenylpyridine) (green), (4,6-F2ppy)$_2$Irpic, PtOEP (platinum(II) octaethylporphyrin), compounds represented by Formula 5, Firpic, TBPe, and the like.

Formula 5

Firpic

TBPe

The dopant may be present in an amount ranging from about 0.1 to about 20 parts by weight based on 100 parts by weight (the total weight of the host and the dopant) of the emitting layer material. In one embodiment, for example, the dopant may be present in an amount ranging from about 0.5 to about 12 parts by weight based on 100 parts by weight (the total weight of the host and the dopant) of the emitting layer material. When the content of the dopant is within these range, phosphorescence and fluorescence concentration quenching can be substantially prevented.

The emitting layer may be formed to a thickness ranging from about 100 to about 1,000 Å. In one embodiment, for example, the emitting layer may be formed to a thickness ranging from about 200 to about 600 Å. When the thickness of the emitting layer is within these ranges, proper emission characteristics can be obtained and increases in driving voltage can be substantially prevented.

When the emitting layer includes a phosphorescent dopant, a hole blocking layer (HBL) (not shown in FIG. 1) may be formed on the emitting layer to prevent diffusion of triplet excitons or holes into the electron transport layer. The hole blocking layer material is not particularly limited, and may be any known hole blocking layer material, e.g., oxadiazole derivatives, triazole derivatives, phenanthroline derivatives, Balq, BCP, and the like.

The hole blocking layer may be formed to a thickness ranging from about 50 to about 1,000 Å. In one embodiment, for example, the hole blocking layer may be formed to a thickness ranging from about 100 to about 300 Å. When the thickness of the hole blocking layer is within these range, proper hole blocking characteristics can be obtained and increases in driving voltage can be substantially prevented.

Next, an electron transport layer (ETL) may be formed using various methods, e.g., vacuum deposition, spin-coating, or casting. When forming the electron transport layer using vacuum deposition or spin-coating, the deposition or coating conditions vary according to the type of compound used, but are generally the same as those for the formation of the hole injection layer.

The electron transport layer material may be an imidazopyrimidine-based compound of Formula 1 as described above and may be used alone or in combination with a known material. Nonlimiting examples of suitable known electron transport layer materials include quinoline derivatives (such as tris(8-quinolinolate)aluminum ($Alq_3$)), and TAZ.

The electron transport layer may be formed to a thickness ranging from about 100 to about 1,000 Å. In one embodiment, for example, the electron transport layer may be formed to a thickness ranging from about 100 to about 500 Å. When the thickness of the electron transport layer is within these range, proper electron transport characteristics can be obtained and increases in driving voltage can be substantially prevented.

An electron injection layer (EIL) may be formed on the electron transport layer to facilitate the injection of electrons from a cathode. The electron injection layer material may be any known electron injection layer material, e.g., LiF, NaCl, CsF, $Li_2O$, or BaO. The deposition or coating conditions of the electron injection layer vary according to the type of compound used, but are generally the same as those for the formation of the hole injection layer.

The electron injection layer may be formed to a thickness ranging from about 1 to about 100 Å. In one embodiment, the electron injection layer may be formed to a thickness ranging from about 5 to about 90 Å. When the thickness of the electron injection layer is within these range, proper electron injection characteristics can be obtained and increases in driving voltage can be substantially prevented.

Finally, a second electrode may be formed on the electron injection layer by vacuum deposition or sputtering. The second electrode may be a cathode or an anode. The material of the second electrode may be a metal or alloy having a low work function, an electroconductive compound, or a mixture thereof. Nonlimiting examples of suitable materials for the second electrode include lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode formed of ITO or IZO to produce a front-emission type device.

The following Synthesis Examples detailing the synthesis of Compounds 1-3 and Examples detailing the manufacturing of organic light-emitting devices employing organic layers including Compounds 1-3 are presented for illustrative purposes only and are not intended to limit the scope of the invention.

EXAMPLES

Synthesis Example 1

Synthesis of Compound 1

Compound 1 was synthesized according to Reaction Scheme 1.

Reaction Scheme 1

1a

-continued

Compound 1

Synthesis of Intermediate 1a

Copper bromide (10 g, 44 mmol) and 2-aminoanthraquinone (8 g, 35.8 mmol) were added to 250 ml of bromic acid, and the reaction mixture was heated to 65° C. When gas generation was stopped, the reaction solution was cooled to room temperature, added to a 20% HCl solution (1,000 ml), and extracted with dichloromethane. The organic layer was dried over anhydrous magnesium sulfate to remove residual moisture, dried under reduced pressure, and purified by column chromatography (dichloromethane/n-hexane=4:1) to yield intermediate 1a (7.7 g).

Synthesis of Intermediate 1b

The intermediate 1a (10 g, 34.8 mmol) was added to 100 ml of dried THF under a nitrogen atmosphere. The reaction mixture was cooled to −78° C., and 2-naphthyl magnesium bromide (0.5M, 10 mmol) was gradually added thereto. The reaction solution was heated to room temperature and stirred for three hours. An ammonium chloride solution was added thereto and the resultant solution was extracted with methylenechloride. The organic layer was dried over anhydrous magnesium sulfate to remove the solvent, and dissolved in a trace amount of ethylether. Petroleum ether was added thereto and the reaction mixture was stirred for several hours to obtain a solid compound. The solid compound was filtered and dried under vacuum to yield dinaphthyl dialcohol (17.6 g).

The dinaphthyl dialcohol (17.6 g, 32.4 mmol) was dispersed in 200 ml of acetic acid under a nitrogen atmosphere, and potassium iodide (53.4 g, 330 mmol) and sodium hypophosphite hydrate (58 g, 660 mmol) were added thereto. The reaction mixture was stirred and refluxed for three hours. The reaction solution was cooled to room temperature, filtered, washed with water and methanol, and dried under vacuum to yield intermediate 1b as a light yellow powder (11.3 g).

Synthesis of Intermediate 1c

The intermediate 1b (5 g, 9.81 mmol) was dissolved in 70 ml of dried THF under a nitrogen atmosphere, and butyl lithium (4.7 ml, 11.8 mmol) was added dropwise thereto at −78° C. The reaction mixture was stirred at −78° C. for one hour, and trimethylborate (2.20 ml, 29.4 mmol) was added thereto. The reaction solution was heated to room temperature and incubated for one hour. Then, a 2N HCl solution was added thereto, and the resultant solution was stirred for three hours. The resultant solid compound was washed and filtered with toluene to yield intermediate 1c as a light yellow powder (3.27 g, yield: 70%).

Synthesis of Intermediate 1d 2-aminopyrimidine (3.39 g, 35.98 mmol) and 2,4'-dibromoacetophenone (10 g, 35.98 mmol) were dissolved in ethanol (150 ml), and the reaction mixture was refluxed for 12 hours. The reaction solution was cooled to room temperature to obtain a white solid. The white solid was washed and filtered with a saturated $NaHCO_3$ solution. The organic layer was dried over anhydrous magnesium sulfate to remove residual moisture, dried under reduced pressure, and recrystallized (in dichloromethane/n-hexane) to yield intermediate 1d as a plate crystal (8.02 g, yield: 82%).

Synthesis of Compound 1

The intermediate 1c (1.85 g, 3.90 mmol) and the intermediate 1d (1 g, 3.90 mmol) were added to a mixed solvent of a potassium carbonate solution (2.7 g, 19.5 mmol) and THF, and $Pd(PPh_3)_4$ (225 mg, 0.196 mmol) was added thereto while stirring. The reaction mixture was refluxed for six hours. The reaction solution was cooled to room temperature, and the resultant solid compound was washed with water, ethanol, and toluene, and filtered to yield Compound 1 as a yellow powder (1.73 g, yield: 71%). (1H NMR (400 MHz, CDCl3) 8.51 (1H), 8.40 (1H), 8.12 (1H), 8.06-7.99 (5H), 7.96 (2H), 7.85 (1H), 7.78-7.59 (15H), 7.32 (2H), 6.84 (1H)).

Synthesis Example 2

Synthesis of Compound 2

Compound 2 (a yellow powder) was synthesized as in Synthesis Example 1 except that phenyl magnesium bromide was used instead of 2-naphthyl magnesium bromide in the synthesis of the intermediate 1b. (1H NMR (400 MHz, CDCl3) 8.54 (1H), 8.42 (1H), 8.07 (2H), 7.96 (1H), 7.83 (1H), 7.80 (1H), 7.73-7.48 (15H), 7.35 (2H), 6.87 (1H)).

Synthesis Example 3

Synthesis of Compound 3

Compound 3 (a yellow powder) was synthesized as in Synthesis Example 1 except that phenyl magnesium bromide was used instead of 2-naphthyl magnesium bromide in the synthesis of the intermediate 1b, and 2,4'-dibromopropiophenone was used instead of dibromoacetophenone in the synthesis of the intermediate 1d. (1H NMR (400 MHz, CDCl3) 8.54 (1H), 8.22 (1H), 7.97 (1H), 7.93 (2H), 7.70 (1H), 7.71-7.52 (15H), 7.35 (2H), 6.92 (1H), 2.73 (3H)).

Example 1

A 15 $\Omega/cm^2$ ITO glass substrate (Corning, 1,200 Å) was cut into 50 mm×50 mm×0.7 mm pieces and subjected to ultrasonic cleaning in isopropyl alcohol and pure water (5 minutes for each) and UV/ozone cleaning (30 minutes) to form anodes. Then, m-MTDATA was vacuum-deposited on the anodes to form hole injection layers with a thickness of 750 Å, and α-NPD was vacuum-deposited on the hole injection layers to form hole transport layers with a thickness of 150 Å. DSA (97 wt %) used as a host and TBPe (3 wt %) used as a dopant were co-deposited on the hole transport layers to form emitting layers with a thickness of 300 Å. Compound 1 obtained in Synthesis Example 1 was vacuum-deposited on the emitting layers to form electron transport layers with a thickness of 200 Å. LiF was vacuum-deposited on the electron transport layers to form electron injection layers with a thickness of 80 Å, and Al was vacuum-deposited on the electron injection layers to form cathodes with a thickness of 3,000 Å, thereby completing the manufacture of organic light-emitting devices.

Example 2

Organic light-emitting devices were manufactured as in Example 1 except that Compound 2 obtained in Synthesis Example 2 was used as an electron transport layer material.

Example 3

Organic light-emitting devices were manufactured as in Example 1 except that Compound 3 obtained in Synthesis Example 3 was used as an electron transport layer material.

Comparative Example 1

Organic light-emitting devices were manufactured as in Example 1 except that Alq3 (8-hydroxyquinoline aluminum complex) was used as an electron transport layer material.

Evaluation Example

The current density (mA/cm$^2$), driving voltage (V), brightness (cd/m$^2$), and efficiency (lm/W) of the organic light-emitting devices manufactured in Examples 1-3 and Comparative Example 1 were evaluated using a PR650 (Spectroscan) Source Measurement Unit (manufactured by PhotoResearch), and the results are presented in Table 1 below.

TABLE 1

| Sample | Current density (mA/cm$^2$) | Driving voltage (V) | Brightness (cd/m$^2$) | Efficiency (lm/W) |
|---|---|---|---|---|
| Example 1 | 10 | 4.1 | 860 | 6.54 |
| Example 2 | 10 | 4.0 | 834 | 6.46 |
| Example 3 | 10 | 4.6 | 771 | 5.28 |
| Comparative Example 1 | 10 | 5.9 | 581 | 2.90 |

As shown in Table 1, the organic light-emitting devices manufactured in Examples 1-3 exhibited better current density, driving voltage, brightness, and efficiency characteristics than the organic light-emitting devices manufactured in Comparative Example 1. These results show that an organic light-emitting device employing an organic layer including an imidazopyrimidine compound of Formula 1 according to embodiments of the present invention exhibit higher brightness, higher efficiency, lower driving voltages, and longer lifetimes than conventional organic light-emitting devices.

The imidazopyrimidine-based compounds of Formula 1 according to embodiments of the present invention have good electron transport capabilities. Thus, organic light-emitting devices employing organic layers including imidazopyrimidine-based compounds can exhibit lower driving voltages, higher brightness, higher efficiency, lower power consumption, and longer lifetimes.

While the present invention has been illustrated and described with reference to certain exemplary embodiments, it will be understood by those of ordinary skill in the art that various changes may be made to the described embodiments without departing from the spirit and scope of the present invention as defined by the following claims.

What is claimed is:

1. An imidazopyrimidine-based compound comprising a compound represented by Formula 1:

Formula 1 wherein,
each of $R_1$, $R_2$, $R_3$, $R_4$, $R_5$, $R_6$, $R_7$, $R_8$, $R_9$, and $R_{10}$ is independently selected from the group consisting of hydrogen, halogens, hydroxy groups, cyano groups, substituted and unsubstituted $C_1$-$C_{30}$ alkyl groups, substituted and unsubstituted $C_1$-$C_{30}$ alkoxy groups, substituted and unsubstituted $C_1$-$C_{30}$ acyl groups, substituted and unsubstituted $C_2$-$C_{30}$ alkenyl groups, substituted and unsubstituted $C_2$-$C_{30}$ alkynyl groups, substituted and unsubstituted $C_6$-$C_{30}$ aryl groups, and substituted and unsubstituted $C_3$-$C_{30}$ heteroaryl groups, wherein at least two adjacent groups selected from the group consisting of $R_4$ through $R_6$ are optionally joined together to form a saturated or unsaturated ring, and wherein at least two adjacent groups selected from the group consisting of $R_8$ through $R_{10}$ are optionally joined together to form a saturated or unsaturated ring;
each of $L_1$ and $L_2$ is independently selected from the group consisting of single bonds, substituted and unsubstituted $C_1$-$C_{30}$ alkylene groups, substituted and unsubstituted $C_6$-$C_{30}$ arylene groups, and substituted and unsubstituted $C_3$-$C_{30}$ heteroarylene groups;
each of $Ar_1$ and $Ar_2$ is independently selected from the group consisting of substituted and unsubstituted $C_6$-$C_{30}$ aryl groups, and substituted and unsubstituted $C_3$-$C_{30}$ heteroaryl groups;
each of p and q is an integer ranging from 1 to 5; and
each of m and n is an integer ranging from 0 to 4, wherein a sum of m and n is not zero.

2. The imidazopyrimidine-based compound of claim 1, wherein each of $R_1$ through $R_{10}$ is independently selected from the group consisting of hydrogen, substituted and unsubstituted $C_1$-$C_{10}$ alkyl groups, substituted and unsubstituted $C_2$-$C_{10}$ alkenyl groups, substituted and unsubstituted $C_6$-$C_{12}$ aryl groups, and substituted and unsubstituted $C_3$-$C_{12}$ heteroaryl groups.

3. The imidazopyrimidine-based compound of claim 1, wherein each of $R_1$ through $R_{10}$ is independently selected from the group consisting of hydrogen, $C_1$-$C_{10}$ alkyl groups, $C_1$-$C_{10}$ haloalkyl groups, $C_2$-$C_{10}$ alkenyl groups, $C_2$-$C_{10}$ haloalkenyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

4. The imidazopyrimidine-based compound of claim 1, wherein at least two adjacent groups selected from the group consisting of $R_4$ through $R_6$ or at least two adjacent groups selected from the group consisting of $R_8$ through $R_{10}$ are joined together to form a substituted or unsubstituted $C_6$-$C_{12}$ aromatic ring.

5. The imidazopyrimidine-based compound of claim 1, wherein each of $L_1$ and $L_2$ is independently selected from the group consisting of substituted and unsubstituted $C_6$-$C_{12}$ arylene groups, and substituted and unsubstituted $C_3$-$C_{12}$ heteroarylene groups.

6. The imidazopyrimidine-based compound of claim 1, wherein each of $L_1$ and $L_2$ is independently selected from the group consisting of phenylene groups, halophenylene groups, $C_1$-$C_{10}$ alkylphenylene groups, $C_1$-$C_{10}$ alkoxyphenylene groups, naphthylene groups, halonaphthylene groups, $C_1$-$C_{10}$ alkylnaphthylene groups, and $C_1$-$C_{10}$ alkoxynaphthylene groups.

7. The imidazopyrimidine-based compound of claim 1, wherein each of $Ar_1$ and $Ar_2$ is independently selected from the group consisting of substituted and unsubstituted $C_6$-$C_{12}$ aryl groups, and substituted and unsubstituted $C_3$-$C_{12}$ heteroaryl groups.

8. The imidazopyrimidine-based compound of claim 1, wherein each of $Ar_1$ and $Ar_2$ is independently selected from the group consisting of phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, $C_1$-$C_{10}$ alkoxynaphthyl groups, pyridinyl groups, halopyridinyl groups, $C_1$-$C_{10}$ alkylpyridinyl groups, $C_1$-$C_{10}$ alkoxypyridinyl groups, quinolinyl groups, haloquinolinyl groups, $C_1$-$C_{10}$ alkylquinolinyl groups, $C_1$-$C_{10}$ alkoxyquinolinyl groups, isoquinolinyl groups, haloisoquinolinyl groups, $C_1$-$C_{10}$ alkylisoquinolinyl groups, and $C_1$-$C_{10}$ alkoxyisoquinolinyl groups.

9. The imidazopyrimidine-based compound of claim 1, wherein m is 0 and n is 1.

10. The imidazopyrimidine-based compound of claim 1, wherein each of m and n is 1.

11. The imidazopyrimidine-based compound of claim 1, wherein the compound represented by Formula 1 is selected from the group consisting of Compounds 1 through 9:

Compound 1

Compound 2

Compound 3

Compound 4

-continued

Compound 5

Compound 6

Compound 7

Compound 8

Compound 9

12. An organic light-emitting device comprising:
a first electrode;
a second electrode; and
an organic layer between the first electrode and the second electrode, the organic layer comprising the imidazopyrimidine-based compound of claim 1.

13. The organic light-emitting device of claim 12, wherein the organic layer is an electron transport layer.

14. The organic light-emitting device of claim 13, further comprising a layer between the first and second electrodes, the layer being selected from the group consisting of hole injection layers, hole transport layers, electron blocking layers, emitting layers, hole blocking layers, electron injection layers, and combinations thereof.

15. The organic light-emitting device of claim 12, wherein the organic layer is an electron transport layer, and the organic light-emitting device further comprises a hole injection layer, a hole transport layer, an emitting layer, and an electron injection layer between the first electrode and the second electrode.

* * * * *